United States Patent
Bergsma et al.

(10) Patent No.: US 10,323,047 B2
(45) Date of Patent: Jun. 18, 2019

(54) PROCESS TO PREPARE ALUMINOXANES

(71) Applicant: Akzo Nobel Chemicals International B.V., Arnhem (NL)

(72) Inventors: Jelle Martin Bergsma, Deventer (NL); Peter Van Der Kruijs, Deventer (NL); Richard Herman Woudenberg, Diepenveen (NL)

(73) Assignee: AKZO NOBEL CHEMICALS INTERNATIONAL B.V., Arnhem (NL)

( * ) Notice: Subject to any disclaimer, the term of this patent is extended or adjusted under 35 U.S.C. 154(b) by 44 days.

(21) Appl. No.: 15/568,507

(22) PCT Filed: Apr. 21, 2016

(86) PCT No.: PCT/EP2016/058818
§ 371 (c)(1),
(2) Date: Oct. 23, 2017

(87) PCT Pub. No.: WO2016/170017
PCT Pub. Date: Oct. 27, 2016

(65) Prior Publication Data
US 2018/0134731 A1 May 17, 2018

(30) Foreign Application Priority Data
Apr. 24, 2015 (EP) .................................... 15165042

(51) Int. Cl.
C07C 2/30 (2006.01)
C08F 10/00 (2006.01)
C07F 5/06 (2006.01)
B01J 31/14 (2006.01)

(52) U.S. Cl.
CPC .............. *C07F 5/068* (2013.01); *B01J 31/143* (2013.01); *C07C 2/30* (2013.01); *C08F 10/00* (2013.01); *B01J 2231/12* (2013.01); *B01J 2231/20* (2013.01); *C07C 2531/14* (2013.01); *Y02P 20/582* (2015.11)

(58) Field of Classification Search
CPC ...... C07F 5/058; B01J 31/143; B01J 2231/12; B01J 2231/20; C07C 2/30; C07C 2531/14; C08F 10/00; Y02P 20/582
USPC ....................................................... 526/189
See application file for complete search history.

(56) References Cited

U.S. PATENT DOCUMENTS

| | | | |
|---|---|---|---|
| 4,055,634 A | 10/1977 | Brenner et al. | |
| 5,329,032 A | 7/1994 | Tran et al. | |
| 5,663,394 A | 9/1997 | Roberg et al. | |
| 5,670,589 A | 9/1997 | Geerts et al. | |
| 5,831,109 A | 11/1998 | Smith et al. | |
| 9,505,788 B2 | 11/2016 | van der Kruijs et al. | |
| 2007/0197745 A1 | 8/2007 | Kaji et al. | |
| 2012/0271087 A1 | 10/2012 | Brown et al. | |

FOREIGN PATENT DOCUMENTS

| | | |
|---|---|---|
| DE | 2507532 A1 | 8/1975 |
| EP | 0 726 271 A1 | 8/1996 |
| EP | 0 874 856 B1 | 11/1998 |
| WO | 97/14699 | 4/1997 |
| WO | 99/47526 | 9/1999 |

OTHER PUBLICATIONS

Kareiva et al., "Carboxylate-Substituted Alumoxanes as Processable Precursors to Transition Metal-Aluminum and Lanthanide-Aluminum Mixed-Metal Oxides" Atomic Scale Mixing via a New Transmetalation Reaction, (Chem. Mater. 1996, vol. 8, No. 9, pp. 2331-2340).*
Baba, Yoshio: "Reactions of Triethylaluminum With Alpha Beta Unsaturated Carbonyl Compounds", Bulletin of the Chemical Society of Japan, vol. 41, No. 4, 1968, pp. 928-931, ISSN: 00009-2673, DOI:10.1246/BCSJ.41.928.
R. Glaser et al., "Thermochemistry of the Initial Steps of Methylaluminoxane Formation. Aluminoxanes and Cycloaluminoxanes by Methane Elimination from Dimethylaluminum deroxide and Its Dimeric Aggregates", JACS, 2011, 133, pp. 13323-13336
H. Sinn et al., "Ziegler-Natta Catalysis", Advances in Organometallic Chemistry, vol. 18, 1980, pp. 99-149.
T. Sugano et al., "Characterization of Alumoxanes by $^{27}$ Al-NMR Spectra", Journal of Molecular Catalysis, vol. 82, Issue 1, Jun. 11, 1993, pp. 93-101
E. Gianetti et al., "Homogeneous Ziegler-Natta Catalysis. II. Ethylene Polymerization by IVB Transition Metal Complexes/Methyl Aluminoxane Catalyst Systems", Journal of Polymer Science: Polymer Chemistry Edition, vol. 23, Issue 8, pp. 2117-2133, Aug. 1985.

(Continued)

*Primary Examiner* — William K Cheung
(74) *Attorney, Agent, or Firm* — Matthew D. Kellam

(57) ABSTRACT

The present invention relates to a process to prepare alkylaluminoxanes by reaction of alkylaluminium with methacrylic acid or a conjugated unsaturated carbonyl-functional compound of the formula (I) wherein each R1 and R2 independently are an aliphatic hydrocarbon group, and R3 independently is the same hydrocarbon group as R1 and R2 or a hydrogen atom, and R4 isanaliphatic hydrocarbon group, a hydroxyl group or a hydrogen atom in the presence of an inert organic solvent. Additionally, it relates to the alkylaluminoxanes obtainable by the above process and their use.

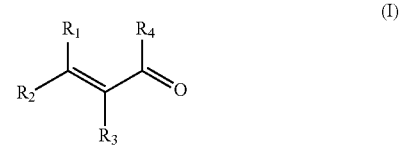

(I)

13 Claims, No Drawings

(56) References Cited

OTHER PUBLICATIONS

S. Pasynkiewicz, "Alumoxanes: Synthesis, Structures, Complexes and Reactions", Polyhedron, vol. 9, Issues 2-3, 1990, pp. 429-453.
H. Winter, "The Preparation of Aluminoxane From Trimethylaluminium at a Defined Surface of Deeply Cooled Ice", Macromol, Symp. 97, pp. 119-125 (1995).
European Search Report issued in EP Application No. 15165042.1 dated Oct. 6, 2015.
International Search Report and Written Opinion for PCT/EP2016/058818 dated Jul. 25, 2016.

\* cited by examiner

PROCESS TO PREPARE ALUMINOXANES

This application is a national stage filing under 35 U.S.C. § 371 of PCT/EP2016/058818, filed Apr. 21, 2016, which claims priority to European Patent Application No. 15165042.1, filed Apr. 24, 2015, the contents of each of which are each incorporated herein by reference in their entirety.

The present invention relates to a novel process to prepare aluminoxanes.

Aluminoxanes are known in the industry, mainly by their application as a catalyst component in polymerization catalysts, especially as a co-catalyst in metallocene catalysts that are used in polymerizing or oligomerizing olefins.

Aluminoxanes (also sometimes referred to as alumoxanes) may be linear, cyclic, oligomeric or polymeric structures wherein two or more aluminium atoms are linked via an oxygen bridge. For example, they have structures like R(—Al(—R)—O)$_n$—Al—R$_2$, wherein n is an integer, each R can independently be an alkyl or alkoxy group, and optionally two or more of the R groups may be linked together to give the indicated cyclic structures, i.e., two R groups can be an oxygen bridge between two aluminium atoms. When at least part of the R groups are methyl groups, the aluminoxane is called a methylaluminoxane (MAO).

Aluminoxanes are described in several documents such as in R Glaser et al., "Thermochemistry of the Initial Steps of Methylaluminoxane Formation. Aluminoxanes and Cycloaluminoxanes by Methane Elimination from Dimethylaluminum Hydroxide and Its Dimeric Aggregates", *JACS*, 2011, 133, 13323-13336; H. Sinn et al., "Ziegler-Natta Catalysis", *Advances in Organometallic Chemistry*, Volume 18, 1980, pp. 99-149; T Sugano et al., "Characterization of alumoxanes by $^{27}$Al-NMR spectra", *Journal of Molecular Catalysis*, Volume 82, Issue 1, 11 Jun. 1993, pp. 93-101; E Gianetti et al., "Homogeneous Ziegler-Natta Catalysis. II. Ethylene polymerization by IVB transition metal complexes/methyl aluminoxane catalyst systems", *Journal of Polymer Science: Polymer Chemistry Edition*, Volume 23, Issue 8, pp. 2117-2134, August 1985; and S. Pasynkiewicz, "Alumoxanes: Synthesis, structures, complexes and reactions", *Polyhedron*, Volume 9, Issues 2-3, 1990, pp. 429-453.

U.S. Pat. No. 5,663,394 discloses a process to prepare methylaluminoxanes. The process involves the reaction of trimethylaluminium with water in an organic solvent. Because of the uncontrollable reactivity of trimethylaluminium with water (also described by H Winter in "The preparation of aluminoxane from trimethylaluminium at a defined surface of deeply cooled ice" in *Macromol. Symp.* 97, 119-125 (1995)), the water reactant can only be underdosed and the reaction in the first instance gives a low conversion. The document in the Examples mentions dosing water in about 0.2 molar ratio to the amount of trimethylaluminium. The process as described in the above U.S. Pat. No. 5,663,394 patent involves an additional step of recycling unreacted trimethylaluminium together with solvent and so concentrating the obtained aluminoxane. At the same time, the reaction between water and trimethylaluminium not only gives the desired aluminoxanes but is also known to give some aluminium salts, like aluminium hydroxide and aluminium oxides, that will precipitate, and gel formation. The gel formation and precipitation problems are known to get worse when TMAL and H$_2$O are dosed closer to equimolar as would be desirable from a reaction yield point of view, and it should be noted that by underdosing the water reactant and the several recycling and concentration steps the above US patent attempts to avoid these problems as much as possible.

The present invention provides an improved process to prepare alkylaluminoxanes with high yield and high conversion that does not require the recycling and separation steps as described for the above state of the art process. In addition, the process of the present invention can be performed in higher concentration, i.e. it can be performed in lower amounts of solvent.

The invention now provides a process to prepare alkylaluminoxanes by reaction of alkylaluminium with methacrylic acid, or a conjugated unsaturated carbonyl-functional compound of the formula (I)

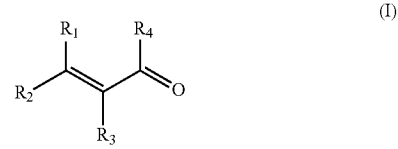

wherein each R1 and R2 independently are an aliphatic hydrocarbon group, and R3 independently is a hydrocarbon group like R1 and R2 but may also be a hydrogen atom, and R4 is a hydrogen atom, an aliphatic hydrocarbon group or a hydroxyl group
in a ratio of 0.1 to 0.8 molar equivalent oxygen atoms in the part —C═O(R4) of the methacrylic acid or conjugated unsaturated carbonyl-functional compound to 1 equivalent of aluminium atoms in the alkylaluminium reactant, and in the presence of an inert organic solvent.

The invention in addition provides the alkylaluminoxanes obtainable by the above process and their use as a component in catalysts used for olefin polymerization or oligomerization processes, such as processes to prepare polyethylene, polypropylene, or rubber. The catalyst in which aluminoxane is used can be a homogeneous or heterogeneous catalyst with or without a support or carrier.

Though the compound of formula (I) is called a carbonyl group-containing compound (or an ene-one compound), it should be realized that if R4 is a hydroxyl group, the compound actually is a conjugated unsaturated carboxylic acid. Depending on whether R4 is a hydrogen atom or an aliphatic hydrocarbon group, the compound is a conjugated unsaturated aldehyde and a ketone, respectively.

The use of several compounds including ketones and carboxylic acids in preparing aluminoxanes has been described in U.S. Pat. No. 5,831,109. The only carboxylic acid and ketone exemplified are benzophenone and benzoic acid, which have an aromatic group instead of the aliphatic group of the compounds of the present invention. These aromatic carbonyl group-containing molecules were found to need much harsher reaction conditions than the carbonyl group-containing molecules of the present invention, if reactive at all.

WO 99/47526 also discloses the use of carbonyl compounds in preparing alkylaluminoxanes in the presence of a catalytic amount of water. The carbonyl compounds are said to be preferably compounds deprived of an enolizable carbon center. Examples of compounds are mentioned but none of them are a conjugated unsaturated carbonyl-functional compound as claimed or methacrylic acid.

US2007/197745 discloses the preparation of alkylaluminoxanes by reaction of alkylaluminium with a oxygen-containing compound that can be a C1-C20 carboxylic acid compound. Concrete examples mentioned include formic acid, acetic acid, propionic acid, n-butyric acid, n-valeric acid, n-caproic acid, n-enanthic acid, n-caprylic acid, n-pelargonic acid, n-capric acid, n-lauric acid, n-myristic acid, n-stearic acid, oxalic acid, malonic acid, succinic acid, glutaric acid, adipic acid, pimelic acid, suberic acid, azelaic acid, sebacic acid, benzoic acid, phthalic acid, citric acid, tartaric acid, lactic acid, malic acid, and toluic acid. Among these, acetic acid, propionic acid, benzoic acid, phthalic acid, toluic acid, and malonic acid are preferred, they are all different carboxylic acids from the conjugated unsaturated carbonyl-functional compounds of the present invention and also were not found to react as beneficially as the ene-one compounds of the present invention.

In the present invention it was found that when reacting alkylaluminium with methacrylic acid or conjugated unsaturated carbonyl-functional compounds of the above specific type, the reaction to give aluminoxanes is gentle and can be better controlled than with water and therefore the alcohol reactant that will deliver the oxygen can be dosed in a higher ratio (than water) to give an improved yield and a lower amount of side products. At the same time, the reaction was found not to be so slow that a lot of energy needs to be added to make it progress. In other words, the present invention provides a process to prepare aluminoxanes with a balanced reactivity between the starting materials. Apart from that, both the aluminium and the oxygen-delivering reagents can be present in a higher amount in the reaction mixture, or in other words, less solvent needs to be used.

The process of the invention is favourable as it does indeed lead to higher conversion, does not require the same number of after-treatment steps like recycling unreacted starting materials and significant amounts of solvent, and also does not require a separation step to remove undesired side products or unreacted reagents.

As an additional advantage, the reaction of the present invention, when compared to using aldehydes, ketones and carboxylic acids that are not according to the invention, was found to proceed under much milder conditions such as a lower temperature. Because the methacrylic acid or conjugated unsaturated carbonyl-functional compounds of the present invention react with alkylaluminium in the reaction to prepare aluminoxanes under milder conditions, the reaction is characterized by a better yield, higher conversion and less side product formation than with other aldehydes, ketones, or carboxylic acids as are state of the art, or water.

For example, when comparing the use of methacrylic acid or mesityl oxide, which are both covered by the present invention, with acetic acid or benzophenone, it was established that acetic acid needs several hours of heating to about 100° C. before a decent conversion is obtained and that the reaction with and benzophenone does not proceed at all under such conditions.

DE 2507532 discloses aluminium-containing molecules that do not possess the Al—O—Al functionality in their structure possessed by aluminoxanes as defined to be the object of the present invention.

The invention in addition in a preferred embodiment relates to a process to prepare alkylaluminoxanes by reaction of alkylaluminium with methacrylic acid or a conjugated unsaturated carbonyl-functional compound of the formula (I)

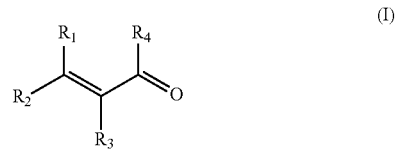

wherein each R1 and R2 independently are an aliphatic hydrocarbon group, and R3 independently is the same hydrocarbon group as R1 and R2 or a hydrogen atom, and R4 is an aliphatic hydrocarbon group, a hydroxyl group or a hydrogen atom, in a ratio of 0.1 to 0.8 molar equivalent oxygen atoms in the part —C=O(R4) of the methacrylic acid or conjugated unsaturated carbonyl-functional compound to 1 equivalent of aluminium atoms in the alkylaluminium reactant, and in the presence of an inert organic solvent containing a carrier, and to the supported aluminoxanes obtainable by this process.

The advantages of the above process and products are that the formed carrier-supported aluminoxanes are more storage stable and less susceptible to gelling. This leads to further advantages when the aluminoxanes need to be further processed later.

In preferred embodiments, the conjugated unsaturated carbonyl-functional compound of the formula (I)

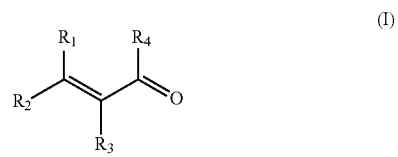

is a compound wherein each R1 and R2 independently are a branched or unbranched aliphatic alkyl or alkylene group, more preferably an alkyl or alkylene group of up to 20 carbon atoms, and R3 independently may be the same alkyl or alkylene group as R1 and R2 but may also be a hydrogen atom. More preferred are conjugated unsaturated carbonyl-functional compounds wherein each R1 and R2 independently are an aliphatic alkyl or alkylene group of up to 8 carbon atoms, even more preferably up to 4 carbon atoms, and wherein R3 independently is an aliphatic alkyl or alkylene group of up to 8 carbon atoms, even more preferably up to 4 carbon atoms, or is a hydrogen atom.

Most preferred conjugated unsaturated carbonyl functional compounds are 3-methyl-2-butenoic acid, 2-methyl-2-propenoic acid, 4-methyl-3-pentene-2-one and 3-methyl-2-butenal.

In preferred embodiments, the alkylaluminium is a trialkylaluminium wherein the alkyl substituents are alkyl groups of up to 8 carbon atoms, more preferably isobutyl, ethyl or methyl. Even more preferred alkylaluminium compounds are compounds wherein at least 20%, even more preferably at least 50%, yet even more preferably at least 80% of the alkyl groups are methyl, like most preferably trimethylaluminium.

In the process of the invention the ratio of reactants is in the range 0.1 to 0.8 molar equivalent oxygen atoms in the part —C=O(R4) of the methacrylic acid or conjugated unsaturated carbonyl-functional compound to 1 equivalent of aluminium atoms in the alkylaluminium reactant.

Preferably, the ratio is between 0.5 and 0.8 molar equivalent, more preferably between 0.6 and 0.75 molar equivalent. This implies that when a carboxylic acid is used wherein R4 adds another oxygen atom, the molar ratio of conjugated unsaturated carbonyl-functional compound to 1 molar equivalent of alkylaluminium is between 0.05 and 0.4, preferably between 0.25 and 0.4, and more preferably between 0.3 and 0.375 molar equivalent.

A ratio of 1:1, as is for instance disclosed in U.S. Pat. No. 4,055,634 and Y. Baba, *Bull Chem. Soc. Japan,* 41 (1968) 928-931, does not lead to the formation of aluminoxanes.

The alkylaluminium in some embodiments of the process is present in an amount of about 1.5 to 20 wt. % aluminium on total reaction mixture, which when using trimethylaluminium corresponds to between about 4 and 54 wt. % trimethylaluminium on total reaction mixture. Preferably, the amount of alkylaluminium is between 5 and 20 wt. %, more preferably 5 and 14 wt. %, on total reaction mixture.

As already indicated above, this means that significantly less solvent needs to be used in the process of the invention when compared to state of the art processes, though it is of course also possible to use more solvent and remove or evaporate it later.

In yet another preferred embodiment of the processes of the invention, in a first step the methacrylic acid or conjugated unsaturated carbonyl-functional compound is dosed to a trialkylaluminium solution in inert solvent, which is next dosed to a suspension of inert solvent optionally containing a carrier, after which further alkylaluminium is added and the resulting reaction mixture (suspension) undergoes a heat treatment.

In a more preferred embodiment in the first step the molar ratio between methacrylic acid or conjugated unsaturated carbonyl-functional compound and trialkylaluminium is between 0.9:1 and 1:0.9 and the additional alkylaluminium that is added is in a molar amount of between 0.2 and 0.6 mole % based on total methacrylic acid or conjugated unsaturated carbonyl-functional compound, preferably ending with a total molar ratio of oxygen atoms in the part —C=O(R4) of the methacrylic acid or conjugated unsaturated carbonyl-functional compound to aluminium atoms of between 0.6 and 0.75 molar equivalent, as indicated above.

In yet another preferred embodiment, the process is operated in the presence of aluminoxane, optionally in a continuous or semi-continuous mode. Even more preferably, the process involves first preparing an alkoxide addition product of the methacrylic acid or conjugated unsaturated carbonyl-functional compound and the alkyl aluminium in an inert organic solvent and (semi-continuously or continuously) adding or dosing this adduct to—previously formed—aluminoxane in an inert organic solvent optionally containing a carrier, or vice versa, though adding or dosing aluminoxane to the adduct is less preferred because it may then be harder to control the reaction. Because the aluminoxane acts as a catalyst in the reaction towards producing (more) aluminoxane, this way of performing the process of the invention is very favourable. Also, performing the reaction this way ensures that the exothermic nature of the reaction can be much better controlled.

As the skilled person will be aware, suitable reaction temperatures during the process are dependent on the choice of starting materials. They are suitably between 0° C. and reflux, in a preferred embodiment between 0 and 100° C., more preferably between 30° C. and 80° C., even more preferably between 40 and 80° C., and most preferably between 50 and 70° C. In some embodiments, it was found beneficial during the process to perform a short heat treatment step of up to 3 hours, preferably 30 to 90 minutes, wherein the temperature is higher than 80° C. up to reflux temperature.

However, when a carrier is present, during the process the reaction mixture is preferably heated to a temperature of higher than 80° C., even more preferably higher than 90° C. In one embodiment the temperature preferably is less than 200° C. An even more preferred way of performing the process in the presence of a carrier is refluxing the mixture in the inert organic solvent.

When, as explained above, an aluminoxane is added as a catalyst, the temperature during the reaction can be somewhat lower again.

The inert organic solvent in which the process of the present invention is performed can be any organic hydrocarbon solvent that the skilled person knows is not reactive with an alkylaluminium compound. Examples thereof are alkanes, such as heptanes, hexanes, or aromates, such as toluene, xylene, ethylbenzene, cumene, mesitylene. Preferably, the solvent is toluene. With inert solvents it is intended to also exclude solvents that are capable of complexing with the aluminium-containing reactants, examples of which are solvents containing an oxygen or nitrogen atom, like ethers such as tetrahydrofuran.

In another embodiment the process of the present invention is performed in the absence of water, preferably less than 1 wt % of water is present, more preferably less than 0.1 wt %, even more preferably less than 0.01 wt % on total solvent.

Examples of the carrier include inorganic or organic support materials, which may be porous support materials and the aluminoxane may be adsorbed or absorbed therein or thereon. Non-limiting examples of suitable supports include compounds comprising Groups 2, 3, 4, 5, 13, and 14 oxides and chlorides. Suitable supports may include, for example, silica, magnesia, titania, zirconia, montmorillonite, phyllosilicate, alumina, silica-alumina, silica-chromium, silica-titania, magnesium chloride, graphite, and the like. Combinations of supports may also be suitable, including, for example, silica-chromium, silica-alumina, silica-titania, and the like. In one embodiment, fumed or calcined silica is a suitable support. The support may possess an average particle size in the range of from about 0.1 to about 90 µm, or from about 1 to about 40 µm, or from about 5 to about 40 µm The support, such as an inorganic oxide, may have a surface area in the range of from about 10 to about 700 m2/g, a pore volume in the range of from about 0.1 to about 4.0 cc/g, and an average particle size in the range of from about 1 to about 500 µm. In some embodiments, the support may have a surface area in the range of from about 50 to about 500 m2/g, a pore volume of from about 0.5 to about 3.5 cc/g, and an average particle size of from about 10 to about 200 µm. In some embodiments, the support may have a surface area in the range of from about 100 to about 400 m2/g, a pore volume from about 0.8 to about 3.0 cc/g, and an average particle size from about 5 to about 100 µm. In some embodiments, the average pore size of the support may be from about 1 to about 50 µm. In some embodiments, the average pore size of the support may be in the range of from about 10 to about 1000 Å, of from about 50 to about 500 Å, or from about 75 to about 350 Å.

The invention is illustrated by the (comparative) Examples below.

EXAMPLES

Comparative Example 1

Benzophenone as Reactant

A 10 ml glass vial equipped with a magnetic stirring bar was charged with 0.8 g toluene and 0.36 g (5.0 mmol) trimethylaluminium (ex AkzoNobel). To this solution, 0.64 g (3.5 mmol) of benzophenone (ex Sigma-Aldrich) dissolved in 0.5 g toluene was slowly added, resulting in an exothermic reaction with gas formation.

$^1$H-NMR analysis of the reaction product after dosing showed multiple peaks in the Al-Me region, which is indicative of the presence of intermediate products. The reaction mixture was left to stir at room temperature for 20 hours.

The mixture was then heated to 105° C. (oil bath) for 1 hour.

$^1$H-NMR analysis showed no significant changes in the composition of the reaction mixture. No formation of aluminoxanes was observed. Even after 16 hours at 105° C. no PMAO was formed.

Comparative Example 2

3-buten-2-one as Reactant

A 30 ml glass vial equipped with a magnetic stirring bar was charged with 8.5 g toluene and 2.7 g (37.5 mmol) trimethylaluminium (ex AkzoNobel). To this solution, 1.05 g (15.0 mmol) of 3-buten-2-one (ex Sigma-Aldrich) was slowly added, resulting in an exothermic reaction with gas formation.

$^1$H-NMR analysis of the reaction product after dosing showed multiple peaks in the Al-Me region, which is indicative of the presence of intermediate products. The reaction mixture was left to stir at room temperature for 20 hours.

The mixture was then heated to 105° C. (oil bath) for 4 hours.

$^1$H-NMR analysis showed no significant changes in the composition of the reaction mixture. No formation of aluminoxanes was observed.

Comparative Example 3

Acetic Acid as Reactant

A 700 ml glass reactor equipped with a mechanical stirrer was charged with 639 g toluene and 25.2 g (0.35 mol) trimethylaluminium (ex AkzoNobel). To this solution, 6.3 g (0.105 mol) of acetic acid (ex Sigma-Aldrich) was slowly dosed, resulting in an exothermic reaction with gas formation.

The mixture was then heated to 105° C. (oil heater/circulator), while monitoring the conversion. After 15 hours at this temperature the conversion was 50% and the aluminoxane turned into a gel.

Comparative Example 4

Acetic Acid as Reactant

A 700 ml glass reactor equipped with a mechanical stirrer was charged with 664 g toluene and 25.2 g (0.35 mol) trimethylaluminium (ex AkzoNobel). To this solution, 2.1 g (35 mmol) of acetic acid (ex Sigma-Aldrich) was slowly dosed, resulting in an exothermic reaction with gas formation.

$^1$H-NMR analysis of the reaction product after dosing showed multiple peaks in the Al-Me region, which is indicative of the presence of intermediate products. The mixture was then heated to 105° C. (oil heater/circulator) for 4 hours.

$^1$H-NMR analysis showed no significant changes in the composition of the reaction mixture. No formation of aluminoxanes was observed.

Example 5

3-methyl-2-butenoic Acid as Reactant

A 10 ml glass vial equipped with a magnetic stirring bar was charged with 1.3 g toluene and 0.36 g (5.0 mmol) trimethylaluminium (ex AkzoNobel). To this solution, 0.18 g (1.8 mmol) of 3-methyl-2-butenoic acid (ex Sigma-Aldrich) was slowly added, resulting in an exothermic reaction with gas formation.

$^1$H-NMR analysis of the reaction product after dosing showed multiple peaks in the Al-Me region, which is indicative of the presence of intermediate products. The reaction mixture was left to stir at room temperature for 20 hours.

The mixture was then heated to 105° C. (oil bath) for 1 hour.

$^1$H-NMR analysis showed that the intermediate peaks disappeared and showed the formation of a broad signal next to the TMAL peak, confirming methylaluminoxane formation.

Example 6

2-methylpropenoic Acid (Methacrylic Acid) as Reactant

A 30 ml glass vial equipped with a magnetic stirring bar was charged with 8.5 g toluene and 2.70 g (37.5 mmol) trimethylaluminium (ex AkzoNobel). To this solution, 0.65 g (7.5 mmol) of 2-methylpropenoic acid (ex Sigma-Aldrich) was slowly added, resulting in an exothermic reaction with gas formation.

$^1$H-NMR analysis of the reaction product after dosing showed multiple peaks in the Al-Me region, which is indicative of the presence of intermediate products. The reaction mixture was left to stir at room temperature for 20 hours.

The mixture was then heated to 105° C. (oil bath) for 1 hour.

$^1$H-NMR analysis showed that the intermediate peaks disappeared and showed the formation of a broad signal next to the TMAL peak, confirming methylaluminoxane formation.

Example 7

3-methyl-2-butenal as Reactant

A 10 ml glass vial equipped with a magnetic stirring bar was charged with 1.3 g toluene and 0.36 g (5.0 mmol) trimethylaluminium (ex AkzoNobel). To this solution, 0.29 g (3.5 mmol) of 3-methyl-2-butenal (ex Sigma-Aldrich) was slowly added, resulting in an exothermic reaction with gas formation.

$^1$H-NMR analysis of the reaction product after dosing showed lots of small peaks in the Al-Me region, which is indicative of the presence of intermediate products. The reaction mixture was left to stir at room temperature for 20 hours.

The mixture was then heated to 105° C. (oil bath) for 1 hour.

$^1$H-NMR analysis showed that the small intermediate peaks disappeared and showed the formation of a broad signal next to the TMAL peak, confirming methylaluminoxane formation.

Example 8

4-methyl-3-pentene-2-one (Mesityl Oxide) as Reactant

A 10 ml glass vial equipped with a magnetic stirring bar was charged with 1.3 g toluene and 0.36 g (5.0 mmol) trimethylaluminium (ex AkzoNobel). To this solution, 0.34 g (3.5 mmol) of 4-methyl-3-penten-2-one (ex Sigma-Aldrich) was slowly added, resulting in an exothermic reaction with gas formation.

$^1$H-NMR analysis of the reaction product after dosing showed multiple peaks in the Al-Me region, which is indicative of the presence of intermediate products. The reaction mixture was left to stir at room temperature for 20 hours.

The mixture was then heated to 105° C. (oil bath) for 1 hour.

$^1$H-NMR analysis showed that the intermediate peaks disappeared and showed the formation of a broad signal next to the TMAL peak, confirming methylaluminoxane formation.

The invention claimed is:

1. Process to prepare alkylaluminoxanes by reaction of alkylaluminium with methacrylic acid or a conjugated unsaturated carbonyl-functional compound of the formula (I)

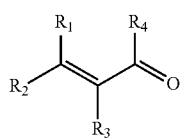

wherein each R1 and R2 independently are an aliphatic hydrocarbon group, and R3 independently is a hydrocarbon group like R1 and R2 or a hydrogen atom, and R4 is an aliphatic hydrocarbon group, a hydrogen atom or a hydroxyl group in a ratio of 0.1 to 0.8 molar equivalent oxygen atoms in the part C=O(R4) of the methacrylic acid or conjugated unsaturated carbonyl-functional compound to 1 equivalent of aluminium atoms in the alkylaluminium reactant, and in the presence of an inert organic solvent.

2. Process of claim 1 wherein each R1 and R2 independently are a branched or unbranched aliphatic alkyl or alkylene group of up to 20 carbon atoms, and wherein R3 independently is a branched or unbranched aliphatic alkyl or alkylene group of up to 20 carbon atoms or a hydrogen atom, and R4 independently is a branched or unbranched aliphatic alkyl or alkylene group of up to 20 carbon atoms, a hydrogen atom, or a hydroxyl group.

3. Process of claim 1 wherein methacrylic acid or one of the conjugated unsaturated carbonyl-functional compounds from the group of 3-methyl-2-butenoic acid, 2-methyl-2-propenoic acid, 4-methyl-3-pentene-2-one, 3-methyl-2-butenal is used.

4. Process of claim 1 wherein the alkylaluminium is a trialkylaluminium wherein the alkyl groups are alkyl groups of up to 8 carbon atoms.

5. Process of claim 4 wherein one or more of the alkyl groups on the alkylaluminium are selected from the group consisting of isobutyl, ethyl and methyl either individually or in combinations thereof.

6. Process of claim 1 wherein the alkylaluminium is a compound wherein at least 50% of the alkyl groups are methyl.

7. Process of claim 1 wherein the alkylaluminium contains trimethylaluminium.

8. Process of claim 1 wherein the organic solvent is selected from the group consisting of alkanes and aromatics, either individually or in combinations thereof.

9. Process of claim 1 wherein the reaction of alkylaluminium with a methacrylic acid or conjugated unsaturated carbonyl-functional compound is performed in the presence of an aluminoxane.

10. Process of claim 1 wherein the inert organic solvent contains a carrier.

11. Process of claim 10 wherein the carrier is selected from the group consisting of silica, magnesia, titania, zirconia, montmorillonite, phyllosilicate, alumina, silica-alumina, silica-chromium, silica-titania, magnesium chloride, graphite, and combinations thereof.

12. Process of claim 1 wherein the organic solvent is an alkane selected from the group consisting of heptanes and hexanes either individually or in combinations thereof.

13. Process of claim 1 wherein the organic solvent is an aromatic selected from the group consisting of toluene, xylene, ethylbenzene, cumene and mesitylene either individually or in combinations thereof.

* * * * *